United States Patent
Amir et al.

[19]

[11] Patent Number: 6,137,116
[45] Date of Patent: Oct. 24, 2000

[54] OPTICAL PROBE FOR SCANNING SURFACES WITHIN CONSTRICTED SPACES

[75] Inventors: Israel Amir, Princeton, N.J.; Kenneth Henry Billingham, Feasterville, Pa.; Dennis J. Fitch, Batavia, Ill.; Frank P. Higgins, West Trenton, N.J.; Frank Joseph Krainaker, Trenton, N.J.; John Burnet Macdonald, Princeton, N.J.

[73] Assignee: Lucent Technologies Inc., Murray Hill, N.J.

[21] Appl. No.: 09/063,795

[22] Filed: Apr. 21, 1998

[51] Int. Cl.[7] ..................................... G01N 21/84
[52] U.S. Cl. ................. 250/559.44; 250/216; 356/376
[58] Field of Search ....................... 250/559.44, 559.08, 250/216, 227.11, 227.23, 306, 341.2, 223 B, 227.29, 227.31; 356/372, 376; 235/462.01, 462.11

[56] References Cited

U.S. PATENT DOCUMENTS 5,813,987  9/1998  Modell et al. ........................ 250/216

*Primary Examiner*—Seungsook Ham
*Assistant Examiner*—Kevin Pyo
*Attorney, Agent, or Firm*—King and Schickli, PLLC

[57] ABSTRACT

An optical probe is positioned between a pair of connectors positioned substantially adjacent to each other so as to read identifying markings on the face or surface of one of the connectors. The optical probe includes a probe head and an illumination device for projecting light substantially parallel to the face of one of the connectors, i.e., a surface being imaged. The illumination device includes a bifurcated fiber optic cable and a pair of prisms positioned so as to illuminate the surface being imaged from opposite directions. A spectral image representative of light scattered by laser etchings on the surface, or light reflected or absorbed by other markings on the surface is projected by a cylindrical mirror through the path of the light from the illumination device to a camera. The camera displays the image of the surface being imaged on a monitor. The probe head is substantially flat and thin so as to fit between the connectors without damaging the connectors. The probe head is also electrically non-conductive so that it can be used while an electronic system utilizing the connectors is operating.

31 Claims, 3 Drawing Sheets

OPTICAL PROBE FOR SCANNING SURFACES WITHIN CONSTRICTED SPACES

BACKGROUND OF THE INVENTION

The present invention relates in general to optical probes, and, more particularly, to optical probes for scanning the surfaces between tightly packed objects.

Printed circuit boards (PCBs) include a variety of components, such as integrated circuit chips, transistors, diodes and connectors. The connectors on a PCB are typically positioned adjacent to one another with little or no space between the connectors. In certain applications, the connectors must be routinely replaced after a given period of time. The vertical surfaces of the connectors facing each other typically include identifying markings, such as a date code, which are used to determine which connectors should be considered for possible replacement or repair. The markings on the connectors may be formed by laser etching the connectors to form pits and burrs which are arranged to form alpha-numeric characters or other symbols. As the markings on the connectors are on the vertical surfaces facing one another, it was necessary in the past to disconnect the connectors to gain access to the markings. Such a procedure is time consuming and requires the entire system to be shut down while the connectors are removed and inspected.

Accordingly, there is a need for an optical probe which may be used to read identifying markings on a surface of a connector which is positioned substantially adjacent to another connector. Preferably, such an optical probe may be used while the system utilizing the connectors is operating. There is a further need for an optical probe to perform optical inspections within highly constricted spaces. There is also a need for such an optical probe which is easy to operate, easy to maintain, and inexpensive to manufacture.

SUMMARY OF THE INVENTION

The present invention meets these needs by providing an optical probe which may be positioned between a pair of connectors positioned substantially adjacent to one another so as to read identifying markings on a face of one of the connectors. The optical probe includes a probe head and an illumination device for projecting light substantially parallel to a face of one of the connectors, i.e., a surface being imaged. The illumination device includes a bifurcated fiber optic cable or a pair of fiber optic cables and a pair of prisms positioned so as to illuminate the surface being imaged from opposite directions. The illumination device applied in this invention generates uniform lighting across the surface of the connector and is appropriate for imaging a broad range of surfaces, such as laser etched surfaces, painted surfaces and planar color differentiated surfaces. Light scattered by the laser etchings or other discontinuities on the surface is projected by a cylindrical mirror through the path of the light from the illumination device to a camera. The probe head is substantially flat and thin so as to fit between the connectors without damaging the connectors. The probe head is also electrically non-conductive so that it can be used while the system utilizing the connectors is operating.

According to a first aspect of the present invention, an optical probe comprises an illumination device, an optical device and a camera. The illumination device projects light substantially parallel to a surface being imaged with a portion of the light being scattered or absorbed by the surface in accordance with its physical or optical characteristics. The scattered or absorbed light forms a spectral image of the surface. The optical device receives the spectral image while the camera is positioned to receive the spectral image from the optical device.

Preferably, the optical device comprises a cylindrical mirror. The illumination device may comprise a light source generating the light, a first fiber optic cable and a first prism. The light source transmits a first portion of the light to the first prism through the first fiber optic cable while the first prism is positioned so as to project the first portion of the light in a first direction substantially parallel to the surface being imaged. The illumination device may further comprise a second fiber optic cable and a second prism. The light source transmits a second portion of the light to the second prism through the second fiber optic cable with the second prism being positioned so as to project the second portion of the light in a second direction substantially parallel to the surface being imaged. Preferably, the first direction is offset from the second direction by approximately 180 degrees. The first and second fiber optic cables are preferably portions of a bifurcated fiber optic cable. The spectral image is representative of the surface being scanned and, more particularly, markings on or in the surface. Preferably, there is a gap of a predetermined distance between the first fiber optic cable and the first prism. The predetermined distance may range from approximately 0.5 inches (1.27 cm) to approximately 1.5 inches (3.81 cm).

According to another aspect of the present invention, an optical probe comprises a frame, a substantially flat probe head coupled to the frame, an illumination device, an optical device and a camera. The illumination device is coupled to the frame and forms a portion of the probe head. The illumination device projects light along at least one path substantially parallel to a surface being imaged with the light being scattered or absorbed by a portion of the surface. The scattered or absorbed light forms a spectral image of the surface being imaged. The optical device receives the spectral image from the surface. The optical device forms a portion of the probe head and is positioned generally adjacent to a first end of the probe head. The camera is positioned to receive the spectral image from the optical device.

Preferably, the first end of the probe head is chamfered. The illumination device may comprise a light source generating the light, a first fiber optic cable coupled to the frame and a first prism forming a portion of the probe head. The light source transmits a first portion of the light to the first prism through the first fiber optic cable with the first prism being positioned so as to project the first portion of the light in a first direction substantially parallel to the surface being imaged. The illumination device may further comprise a second fiber optic cable coupled to the frame and a second prism forming a portion of the probe head. The light source transmits a second portion of the light to the second prism through the second fiber optic cable with the second prism being positioned so as to project the second portion of the light in a second direction substantially parallel to the surface being imaged. Preferably, the first direction is offset from the second direction by approximately 180 degrees.

The first and second optical cables are preferably coupled to opposite sides of the frame while the camera is coupled to the frame, as illustrated, generally centered within the frame. The optical device may comprise a cylindrical mirror. To conserve space, the cylindrical mirror is positioned so that the spectral image is transmitted back towards the camera across the path of the light from the illumination device. The cylindrical mirror preferably does not extend beyond an outer plane of the probe head which is substantially parallel to the surface being imaged. The probe head may be less than or equal to about 0.062 inches (0.157 cm) in thickness. Preferably, the probe head is electrically non-conductive and detachably coupled to the frame. The spectral image is representative of markings on or in the surface being imaged.

According to yet another aspect of the present invention, an optical inspection system is provided comprising an optical probe and a display system. The optical probe comprises a frame, a substantially flat probe head coupled to the frame, an illumination device, an optical device and a camera. The illumination device is coupled to the frame and forms a portion of the probe head. The illumination device projects light along at least one path substantially parallel to a surface being imaged with the light being scattered or absorbed by a portion of the surface. The scattered or absorbed light forms a spectral image of the surface being imaged. The optical device receives the spectral image. The optical device is coupled to the probe head and positioned generally adjacent to a first end of the probe head. The camera is positioned to receive the spectral image from the optical device and is configured to generate signals in response to the spectral image. The display system displays an image of the surface being imaged in response to signals from the camera.

The spectral image received by the camera represents an inverted image of the surface being imaged with the display system being configured to invert the inverted image so that the image displayed by the display system is non-inverted. Preferably, the illumination device projects a first portion of the light in a first direction and a second portion of the light in a second direction with the first direction being offset from the second direction by approximately 180 degrees. The probe head is preferably electrically non-conductive. Preferably, the probe head is detachably coupled to the frame.

According to a further embodiment of the present invention, a method of imaging a surface of an object is provided. An optical probe is provided which comprises a frame, a substantially flat probe head coupled to the frame, an illumination device, an optical device and a camera. The illumination device is coupled to the frame and forms a portion of the probe head. The illumination device projects light along at least a first path substantially parallel to a surface of the probe head. An optical device is coupled to the probe head and positioned generally adjacent to a first end of the probe head. The camera is positioned to receive light from the optical device. The probe head of the optical probe is positioned between a pair of substantially adjacent objects such that light from the illumination device is substantially parallel to at least one of two opposing surfaces of the pair of substantially adjacent objects. The optical device receives a spectral image representative of light scattered from or absorbed by one of the two opposing surfaces. One of two opposing surfaces of the pair of substantially adjacent objects is imaged.

The optical device may comprise a cylindrical mirror and the positioning of the probe head of the optical probe between a pair of substantially adjacent objects is performed so that the spectral image is transmitted back across the first path of the light from the illumination device towards the camera. Imaging one of the two opposing surfaces of the pair of substantially adjacent surfaces presents an inverted image to the camera.

Accordingly, it is an object of the present invention to provide an optical probe which may be used to read the identifying markings on the surface of a connector which is positioned substantially adjacent to another connector. It is another object of the present invention to provide such an optical probe which may be used while a system utilizing the connectors is operating. It is yet another object of the present invention to provide an optical probe to perform optical inspections within highly constricted spaces. It is a further object of the present invention to provide an optical probe which is easy to operate, easy to maintain, and inexpensive to manufacture. Other features and advantages of the invention will be apparent from the following description, the accompanying drawings and the appended claims.

DETAILED DESCRIPTION OF THE INVENTION

Figure 1:
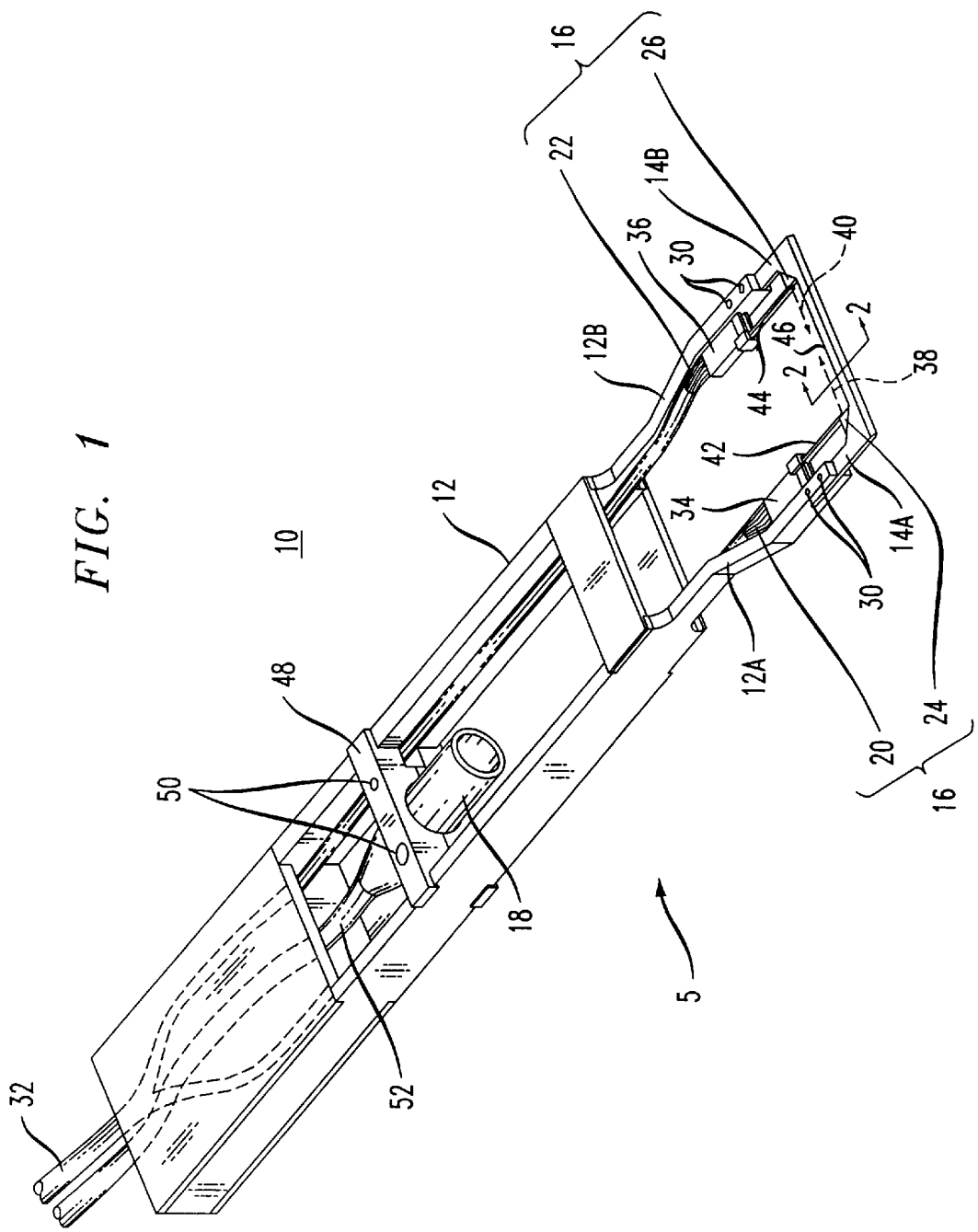
FIG. 1 is a perspective view of an optical probe according to the present invention.
Figure 2:
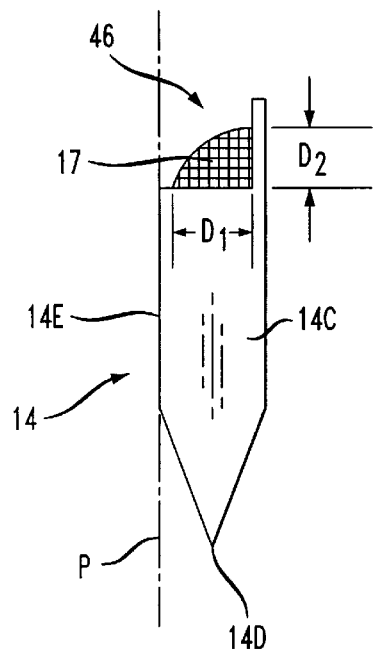
FIG. 2 is a cross-sectional view a head portion of the optical probe taken along section line 2—2 in FIG. 1.
Figure 3:
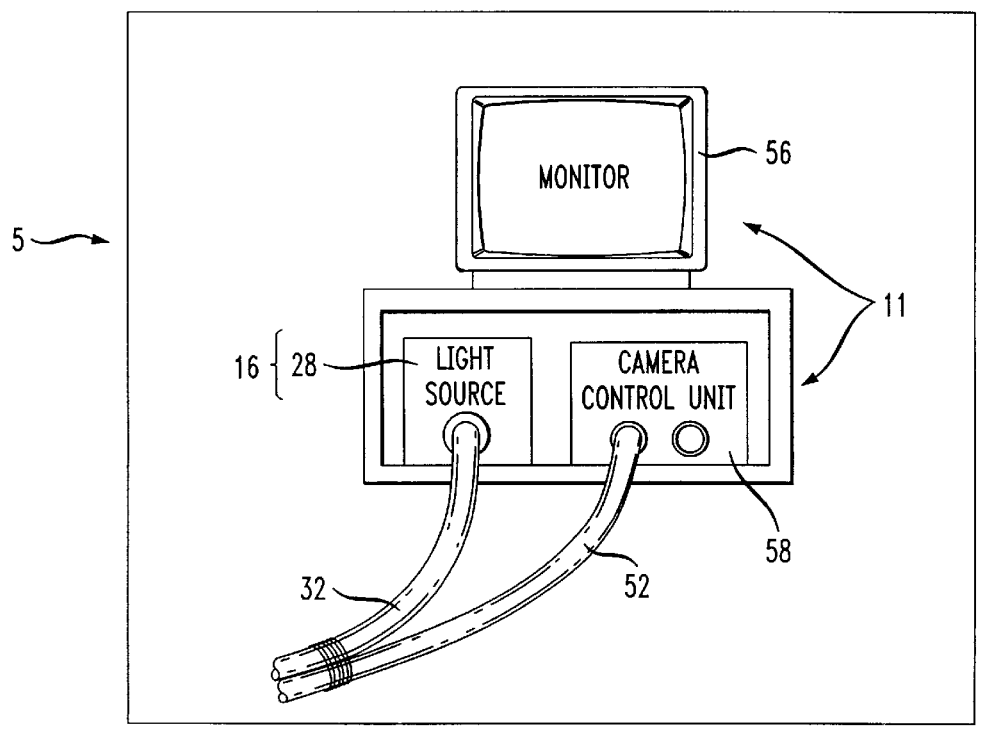
FIG. 3 is a block diagram of a light source and display system used with the optical probe of FIG. 1.

While the present invention is applicable in general to optical probes for performing inspections of devices and surfaces in restricted areas, it will be described herein with reference to an optical probe for inspecting the surface of a connector which is positioned substantially adjacent to another connecter for which the optical probe is particularly attractive and is initially being utilized. Referring to FIGS. 1–3, an optical inspection system 5 is provided comprising an optical probe 10 and a display system 11. The optical probe 10 comprises a frame 12, a probe head 14, an illumination device 16, an optical device 17 (see FIG. 2) and a camera 18. The illumination device 16 includes a first fiber optic cable 20, a second fiber optic cable 22, a first prism 24, a second prism 26 and a light source 28 (see FIG. 3).

Figure 4:
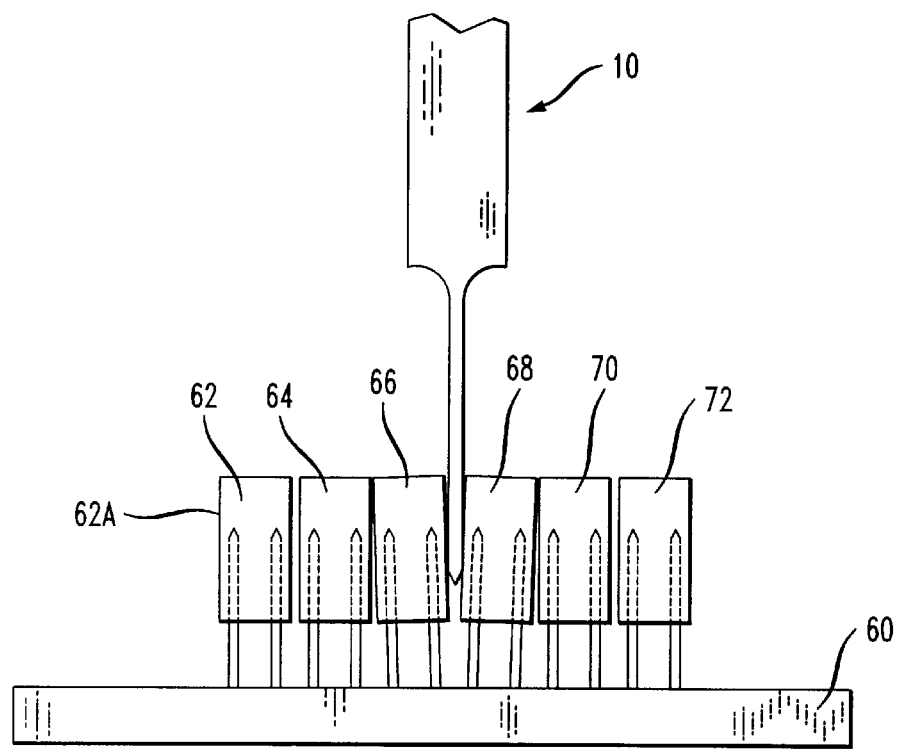
FIG. 4 is a side view of a printed circuit board with a plurality of connectors mounted thereon and the optical probe of FIG. 1 being used with the connectors.

Referring to FIG. 1, the probe head 14 is substantially flat and includes a first arm 14A, a second arm 14B and a head portion 14C. The first and second arms 14A, 14B of the probe head are sized to engage corresponding first and second arms 12A, 128 of the frame 12. The probe head 14 is detachably coupled to the frame 12 through removable dowels 30 for ease of replacement. A first end or leading edge 14D of the probe head 14 is chamfered to act as a wedge to facilitate insertion of probe head 14 between adjacent connectors as shown in FIG. 4. In the illustrated embodiment, the thickness of the head portion 14C of the probe head 14 is about 0.062 inches (0.157 cm). It will be appreciated by those skilled in the art that the thickness of the head portion 14C may vary depending upon the particular application. The probe head 14 is constructed of electrically non-conductive material of sufficient strength to withstand insertion forces of approximately 100 lbs. For example, FR4 epoxy-fiber material was used in a working embodiment.

The first fiber optic cable 20 is coupled to the side of the first arm 12A of the frame 12 while the second fiber optic cable 22 is coupled to the side of the second arm 12B of the frame 12 using conventional fastening methods. In the illustrated embodiment, the first and second fiber optic cables 20 and 22 bifurcated from a main fiber optic cable 32, i.e., the first and second fiber optic cables 20 and 22 split from the main fiber optic cable 32. The main fiber optic cable 32 is coupled to the light source 28. It should be apparent that each of the first and second fiber optic cables 20, 22 are made up of a plurality of individual optical fibers (not shown). Bifurcation conveniently allows the light to be transmitted to the main fiber optic cable 32 and split to the first and second fiber optic cables 20, 22.

The main fiber optic cable 32 includes the sum total of the fibers in each of the first and second fiber optic cables 20, 22 with approximately half of the fibers being randomly routed to the first fiber optic cable 20 and the remaining fibers being routed to the second fiber optic cable 22. A first portion of the light generated by the light source 28 is transmitted through the first fiber optic cable 20 while a second portion of the generated light is transmitted through the second fiber optic cable 22. Accordingly, only one connection to the light source 28 is needed with the net result being that the intensity of light in the first and second fiber optic cables 20 and 22 is substantially uniform. However, it will be appreciated by those skilled in the art that the first and second fiber optic cables 20, 22 may be separate and distinct and coupled directly to the light source 28.

In the illustrated embodiment, light is generated by the light source 28 using a conventional quartz halogen lamp with a power rating of approximately 150 watts. An infrared blocking filter (not shown) is positioned between the light source 28 and the main fiber optic cable 32 to reduce the transmission of heat from the quartz halogen lamp to the fiber optic cable. It will be appreciated by those skilled in the art that other light sources may be used to generate the light needed to illuminate the surface being imaged.

The fibers in the first and second fiber optic cables 20, 22 are grouped to have generally circular cross-sections which transition into rectangular cross-sections near the end of the cables 20, 22. The ends of the fibers are ground and polished to launch substantially parallel light beams towards the first and second prisms 24, 26. The end of the fibers in the first and second fiber optic cables 20, 22 are secured and terminate in respective first and second boxes 34, 36. The first and second prisms 24, 26 form part of the probe head 14 and are positioned adjacent to the first and second arms 14A, 14B, respectively. The first and second prisms 24, 26 are positioned to project the substantially parallel light from the first and second fiber optic cables 20, 22 at an angle of approximately 90 degrees so that the light is substantially parallel to the head portion 14C of the probe head 14. It will be appreciated by those skilled in the art that other optical components, such as mirrors or specular surface coatings, may be used in place of the prisms 24, 26 to project the light received from the fiber optic cables.

In the illustrated embodiment, there is a gap of a predetermined distance between the first and second prisms 24, 26 and the ends of the fibers in the first and second fiber optic cables 20, 22, respectively, with the gap being selected to enhance the uniformity of the light being projected across the surface being imaged. In a working embodiment of the present invention, the predetermined distance may range from approximately 0.5 inches (1.27 cm) to approximately 1.5 inches (3.81 cm). The light transmitted from the cables 20, 22 is therefore substantially uniform upon reaching the surfaces of the prisms 24, 26 such that the light ultimately projected by the prisms 24, 26 is also substantially uniform. However, it will be appreciated by those skilled in the art that the fibers may be coupled directly to the first and second prisms 24, 26 via optical couplers, albeit with less uniformity. The probe head 14 also includes first and second light blockers 42, 44 positioned between respective boxes 34, 36 and prisms 24, 26 to reduce the quantity of extraneous light reaching the optical device 17 the surfaces being inspected.

The illumination device 16 is configured so that the light from the light source 28 is projected in a first direction 38 by the first prism 24 and a second direction 40 by the second prism 26. As shown in FIG. 1, the first and second prisms 24, 26 are positioned so that the light is projected in opposite directions towards each other. The first and second directions are thus offset from each other by about 180 degrees. The uniformity of the light projected along the head portion 14C and the surface being imaged is enhanced by projecting light from opposite directions.

Referring now to FIG. 2, the optical device 17 forms a portion of the probe head 14. A front face 14E of the head portion 14C of the probe head 14 includes a cut-out portion 46 sized and configured to receive the optical device 17. In the illustrated embodiment, the optical device 17 is a cylindrical mirror. However, it will be appreciated by those skilled in the art that the optical device may comprise other optical components.

A first dimension $D_1$ of the cylindrical mirror 17 generally perpendicular to a plane P of the probe head 14 defined by the substantially flat front face 14E of the head portion 14C is less than the thickness of the head portion 14C so that the mirror 17 does not extend beyond the plane P. In the illustrated embodiment, the first dimension $D_1$ of the cylindrical mirror 17 is about 0.050 inches (0.127 cm). A second dimension $D_2$ of the cylindrical mirror 17 generally parallel to the plane P is less than the first dimension $D_1$. The second dimension $D_2$ is approximately 0.038 inches (0.097 cm). However, it will be appreciated by those skilled in the art that the first and second dimensions $D_1$, $D_2$ may vary and may even be equal as long as the cylindrical mirror 17 does not extend beyond the plane P. The length of the mirror 17 may vary depending on the desired field of view and the particular application. In the illustrated embodiment, the cylindrical mirror 17 is approximately 1.5 inches (3.81 cm) in length. The cylindrical mirror 17 is composed of highly polished steel so that it is highly reflective. It will be appreciated by those skilled in the art that other materials may be used to form the cylindrical mirror 17.

Referring again to FIG. 1, the camera 18 is coupled to the frame 12 by a clamping ring 48 and conventional fasteners 50. While a variety of cameras can be used in the present invention, in the illustrated embodiment, the camera 18 is a standard miniature camera model number ME411E commercially available from ELMO. The camera 18 is positioned so that it has the desired field of view and is focused near the cylindrical mirror 17. Referring to FIGS. 1 and 2, the camera 18 includes a cable 52 for transmitting signals representative of the image received from the cylindrical mirror 17 to the display system 11. The display system 11 includes a monitor 56 and a control unit 58. The cable 52 is coupled to the control unit 58 which in turn is coupled to the monitor 56. The monitor 56 displays a visual representation of the image transmitted by the camera 18. The configuration of the mirror 17 results in an inverted, demagnified image. The camera 18 and the monitor 56 are configured to compensate for the inversion and de-magnification caused by the mirror 17 so that the actual image displayed by the monitor 56 is non-inverted and appropriately magnified for ease of viewing. Inversion and magnification is accomplished by reversing the monitor Y-deflection coil connections and expanding the monitor Y-deflection aperture about the monitor field center. In the illustrated embodiment, the monitor 56 is a 14" television monitor model number TM-123U commercially available from JVC. It will be appreciated by those skilled in the art that other television monitors and video monitors may be used.

Figure 5:
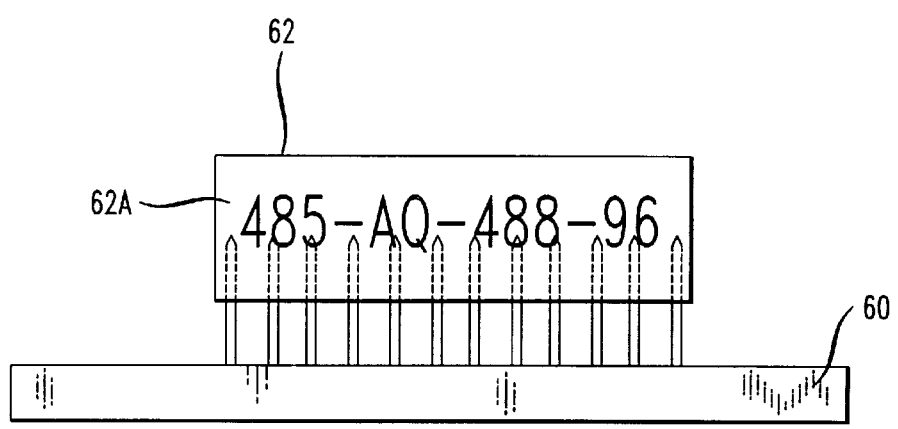
FIG. 5 is a front view of the printed circuit board of FIG. 4 showing representative markings on the side on one of the connectors.

Referring now to FIGS. 4 and 5, the operation of the optical inspection system 5 will be described. FIG. 4 illustrates a printed circuit board 60 having a plurality of connectors 62–72 mounted thereon. The connectors 62–72 are tightly packed on the printed circuit board 60 such that there is little to no gap between each of the substantially adjacent connectors. One or both adjacent faces or surfaces of the connectors 62–72 include identifying markings. A representative marking is shown on a face or surface 62A of the connector 62 in FIG. 5. In the illustrated embodiment, the identifying markings are laser etched into the faces of the connectors resulting in formation of pits and burrs representative of the desired characters.

As shown in FIG. 4, the optical probe 10 and the probe head 14 are held normal to the printed wiring board 60 with the leading edge 14D of the probe head 14 being inserted between the substantially adjacent connectors under inspection. As the probe head 14 is substantially flat and narrow, it is able to squeeze between the connectors to inspect the faces of the connectors. The probe head 14 is positioned so that the cylindrical mirror 17 passes completely past the identifying markings. The first and second portions of the light reflected by the first and second prisms 24, 26 are projected on a path which is substantially parallel to the surface being inspected. The laser etched markings cause the light to be scattered. At least a portion of this scattered light forms a spectral image that is transmitted back across the path of light projected by the prisms 24, 26 to the cylindrical mirror 17 which reflects the spectral image toward the camera 18. The spectral image reflected by the mirror 17 represents an image of the surface of the connector being inspected. The camera 18 generates a signal representative of the image and transmits the signal to the display system 11. The image or identifying markings are displayed on the monitor 56. Preferably, the cylindrical mirror 17 and the camera 18 are configured so that the field of view encompasses substantially the entire marked surface of the connector.

As the probe head 14 is electrically non-conductive, the optical inspection system 5 may be used while the printed circuit board 60 and the system utilizing the printed circuit board 60 is electrically active and functioning. Further, as the probe head 14 is narrow, the probe head 14 may be inserted between the closely packed connectors 62–72 without damaging the connectors or the probe head 14. However, if the probe head 14 is damaged, it can be readily replaced with a new probe head. While the optical inspection system 5 is particularly suited for reading markings that are laser etched into the side of a connector, the optical inspection system 5 may also be used to read markings that are painted or otherwise placed on the side of a connector to produce optical or spectral discontinuities in the otherwise substantially specular surface. In any event, as the light is substantially parallel to the surface being imaged, any surface or spectral discontinuities will create an image of the connector surface markings. It should be apparent that the spectral discontinuities may result from planar color differentiated surfaces, i.e., smooth surfaces where information is imprinted by different color materials. In those situations, the light is partially absorbed by the surface being imaged thereby forming a spectral image. The optical probe 10 may also be used to image other tightly packed objects or objects located in restricted areas.

Having described the invention in detail and by reference to preferred embodiments thereof, it will be apparent that modifications and variations are possible without departing from the scope of the invention defined in the appended claims.

What is claimed is:

1. An optical probe comprising:
   an illumination device projecting light substantially parallel to an entire surface being imaged, a portion of said light being scattered or absorbed by said surface and resulting in a spectral image of said surface;
   an optical device receiving said spectral image; and
   a camera positioned to receive said spectral image from said optical device, wherein said optical probe comprises said illumination device, said optical device, and said camera.

2. The optical probe of claim 1, wherein said optical device comprises a cylindrical mirror.

3. The optical probe of claim 1, wherein said illumination device comprises a light source generating said light, a first fiber optic cable and a first prism, said light source transmitting a first portion of said light to said first prism through said first fiber optic cable, said first prism being positioned so as to project said first portion of said light in a first direction substantially parallel to said surface being imaged.

4. The optical probe of claim 3, wherein said illumination device further comprises a second fiber optic cable and a second prism, said light source transmitting a second portion of said light to said second prism through said second fiber optic cable, said second prism being positioned so as to project said second portion of said light in a second direction substantially parallel to said surface being imaged.

5. The optical probe of claim 4, wherein said first direction is offset from said second direction by approximately 180 degrees.

6. The optical probe of claim 4, wherein said first and second fiber optic cables are portions of a bifurcated fiber optic cable.

7. The optical probe of claim 1, wherein said spectral image is representative of said surface being scanned.

8. The optical probe of claim 3, wherein there is a gap of a predetermined distance between said first fiber optic cable and said first prism.

9. The optical probe of claim 8, wherein said predetermined distance ranges from approximately 0.5 inches (1.27 cm) to approximately 1.5 inches (3.81 cm).

10. An optical probe comprising:
    a frame;
    a substantially flat probe head coupled to said frame;
    an illumination device coupled to said frame, forming a portion of said probe head and projecting light along at least one path substantially parallel to a surface being imaged, a portion of said light being scattered or absorbed by said surface and resulting in a spectral image;
    an optical device receiving said spectral image and being positioned generally adjacent to a first end of said probe head; and
    a camera positioned to receive said spectral image from said optical device.

11. The optical probe of claim 10, wherein said first end of said probe head is chamfered.

12. The optical probe of claim 10, wherein said illumination device comprises a light source generating said light, a first fiber optic cable coupled to said frame and a first prism forming a portion of said probe head, said light source transmitting a first portion of said light to said first prism through said first fiber optic cable, said first prism being positioned so as to project said first portion of said light in a first direction substantially parallel to said surface being imaged.

13. The optical probe of claim 12, wherein said illumination device further comprises a second fiber optic cable coupled to said frame and a second prism forming a portion of said probe head, said light source transmitting a second portion of said light to said second prism through said second fiber optic cable, said second prism being positioned so as to project said second portion of said light in a second direction substantially parallel to said surface being imaged.

14. The optical probe of claim 13, wherein said first direction is offset from said second direction by approximately 180 degrees.

15. The optical probe of claim 13, wherein said first and second optical cables are coupled to opposite sides of said frame.

16. The optical probe of claim 10, wherein said camera is coupled to said frame.

17. The optical probe of claim 10, wherein said optical device comprises a cylindrical mirror.

18. The optical probe of claim 17, wherein said cylindrical mirror is positioned so that said spectral image is transmitted back towards said camera across said at least one path of said light from said illumination device.

19. The optical probe of claim 17, wherein said cylindrical mirror does not extend beyond a plane of said probe head, said plane being substantially parallel to said surface being imaged.

20. The optical probe of claim 10, wherein said probe head is less than or equal to about 0.062 inches (0.157 cm) in thickness.

21. The optical probe of claim 10, wherein said probe head is electrically non-conductive.

22. The optical probe of claim 10, wherein said probe head is detachably coupled to said frame.

23. The optical probe of claim 10, wherein said spectral image is representative of said surface being imaged.

24. An optical inspection system comprising:
   an optical probe; and
   a display system;
   wherein said optical probe comprises:
      a frame;
      a substantially flat probe head coupled to said frame;
      an illumination device coupled to said frame, forming a portion of said probe head and projecting light along at least one path substantially parallel to a surface being imaged, a portion of said light being scattered or absorbed by said surface light and resulting in a spectral image;
      an optical device receiving said spectral image, said optical device being coupled to said probe head and positioned generally adjacent to a first end of said probe head; and
      a camera positioned to receive said spectral image from said optical device and configured to generate signals in response to said spectral image;
   and wherein said display system displays an image of said surface being imaged in response to signals from said camera.

25. The optical inspection system of claim 24, wherein said spectral image received by said camera represents an inverted image of said surface being imaged and wherein said display system is configured to invert said inverted image so that said image displayed by said display system is non-inverted.

26. The optical inspection system of claim 24, wherein said illumination device projects a first portion of said light in a first direction and a second portion of said light in a second direction, said first direction being offset from said second direction by approximately 180 degrees.

27. The optical inspection system of claim 24, wherein said probe head is electrically non-conductive.

28. The optical inspection system of claim 24, wherein said probe head is detachably coupled to said frame.

29. A method of imaging a surface of an object comprising the steps of:
   providing an optical probe comprising:
      a frame;
      a substantially flat probe head coupled to said frame;
      an illumination device coupled to said frame, forming a portion of said probe head and projecting light along at least a first path substantially parallel to a surface of said probe head;
      an optical device coupled to said probe head and positioned generally adjacent to a first end of said probe head; and
      a camera positioned to receive light from said optical device;
   positioning said probe head of said optical probe between a pair of substantially adjacent objects such that light from said illumination device is substantially parallel to at least one of two opposing surfaces of said pair of substantially adjacent objects, said light being scattered or absorbed by one of said two opposing surfaces and forming a spectral image thereof; and
   imaging said one of two opposing surfaces of said pair of substantially adjacent objects.

30. The method of claim 29, wherein said optical device comprises a cylindrical mirror and wherein said step of positioning said probe head of said optical probe between a pair of substantially adjacent objects comprises the step of positioning said probe head such that said spectral image is transmitted back across said at least first path of said light from said illumination device towards said camera.

31. The method of claim 29, wherein said step of imaging said one of two opposing surfaces of said pair of substantially adjacent surfaces comprises the step of inverting said spectral image detected by said camera.

* * * * *